(12) United States Patent
Holroyd

(10) Patent No.: US 7,637,260 B2
(45) Date of Patent: *Dec. 29, 2009

(54) MEDICAMENT DISPENSING DEVICE WITH A MULTIMATERIAL DIAPHRAGM BOUNDING A PNEUMATIC FORCE CHAMBER

(75) Inventor: Michael Holroyd, Cambridge (GB)

(73) Assignee: Norton Healthcare Limited, London (GB)

( * ) Notice: Subject to any disclaimer, the term of this patent is extended or adjusted under 35 U.S.C. 154(b) by 337 days.

This patent is subject to a terminal disclaimer.

(21) Appl. No.: 10/276,531

(22) PCT Filed: Jun. 8, 2001

(86) PCT No.: PCT/US01/18664

§ 371 (c)(1), (2), (4) Date: Jul. 14, 2003

(87) PCT Pub. No.: WO01/93933

PCT Pub. Date: Dec. 13, 2001

(65) Prior Publication Data

US 2004/0025867 A1 Feb. 12, 2004

Related U.S. Application Data

(63) Continuation-in-part of application No. 09/591,321, filed on Jun. 9, 2000, now Pat. No. 6,553,988.

(51) Int. Cl.
*A61M 11/00* (2006.01)
(52) U.S. Cl. ............... 128/200.23; 128/200.14
(58) Field of Classification Search ............ 128/200.23, 128/200.14, 203.15, 200.18, 200.21, 205.24, 128/200.22, 203.24, 204.26, 203.23
See application file for complete search history.

(56) References Cited

U.S. PATENT DOCUMENTS

| | | | |
|---|---|---|---|
| 2,638,127 | A | 5/1953 | Griswold |
| 3,456,645 | A | 7/1969 | Brock |
| 3,506,004 | A | 4/1970 | Mann et al. |
| 3,565,070 | A | 2/1971 | Hanson et al. |
| 3,598,294 | A | 8/1971 | Hendrick et al. |
| 3,605,738 | A | 9/1971 | Ciranna |
| 3,702,114 | A | 11/1972 | Zacarian |
| 3,789,843 | A | 2/1974 | Armstrong, et al. |

(Continued)

FOREIGN PATENT DOCUMENTS

EP 0023409 2/1981

(Continued)

*Primary Examiner*—Justine R Yu
*Assistant Examiner*—Annette F Dixon
(74) *Attorney, Agent, or Firm*—RatnerPrestia

(57) ABSTRACT

A metered dose inhaler for use with a pressurized aerosol container which is preferably breath-actuated. A preload is applied to the internal aerosol valve by an amount sufficient to result in a dose release, but this is prevented by the application of a pneumatic resisting force. The inhaler comprises a release device which, upon actuation, releases the resisting force and allows the preload to actuate the aerosol valve. A metered dose of medicament is then released for inhalation by the patient. The pneumatic resisting force is established by a negative pressure region defined in part by a diaphragm. The diaphragm includes a central disk of a first, relatively high stiffness material and a peripheral ring, coupled by a flexure of a second, relatively low stiffness material.

12 Claims, 3 Drawing Sheets

U.S. PATENT DOCUMENTS

| | | | |
|---|---|---|---|
| 4,414,972 A | 11/1983 | Young et al. | |
| 4,648,393 A | 3/1987 | Landis et al. | |
| 4,805,978 A | 2/1989 | Bruch et al. | |
| 5,027,808 A | 7/1991 | Rich et al. | |
| 5,069,204 A | 12/1991 | Smith et al. | |
| 5,119,806 A | 6/1992 | Palson et al. | |
| 5,184,761 A | 2/1993 | Lee | |
| 5,217,004 A | 6/1993 | Blasnik et al. | |
| 5,224,472 A | 7/1993 | Pesenti et al. | |
| 5,447,150 A * | 9/1995 | Bacon | 128/200.14 |
| 5,447,550 A | 9/1995 | Leal-Cantu et al. | |
| 5,727,546 A | 3/1998 | Clarke et al. | |
| 5,772,190 A | 6/1998 | May et al. | |
| 6,189,904 B1 | 2/2001 | Gentry et al. | |
| 6,354,577 B1 | 3/2002 | Quintile et al. | |
| 6,553,988 B1 * | 4/2003 | Holroyd | 128/200.23 |

FOREIGN PATENT DOCUMENTS

| | | |
|---|---|---|
| EP | 0045419 | 10/1984 |
| EP | 0186280 | 7/1986 |
| GB | 1269554 | 4/1972 |
| GB | 1269811 | 4/1972 |
| GB | 1288971 | 9/1972 |
| GB | 1297993 | 11/1972 |
| GB | 1335378 | 10/1973 |
| GB | 1383761 | 2/1974 |
| GB | 1392192 | 4/1975 |
| GB | 1392193 | 4/1975 |
| GB | 1413285 | 11/1975 |
| GB | 22047991 | 11/1988 |
| GB | 2263873 | 8/1993 |
| GB | 2264238 | 8/1993 |
| GB | 2344534 | 6/2000 |
| GB | 2344535 | 6/2000 |
| WO | WO85/01880 | 5/1985 |
| WO | WO 93/24167 | 12/1993 |

* cited by examiner

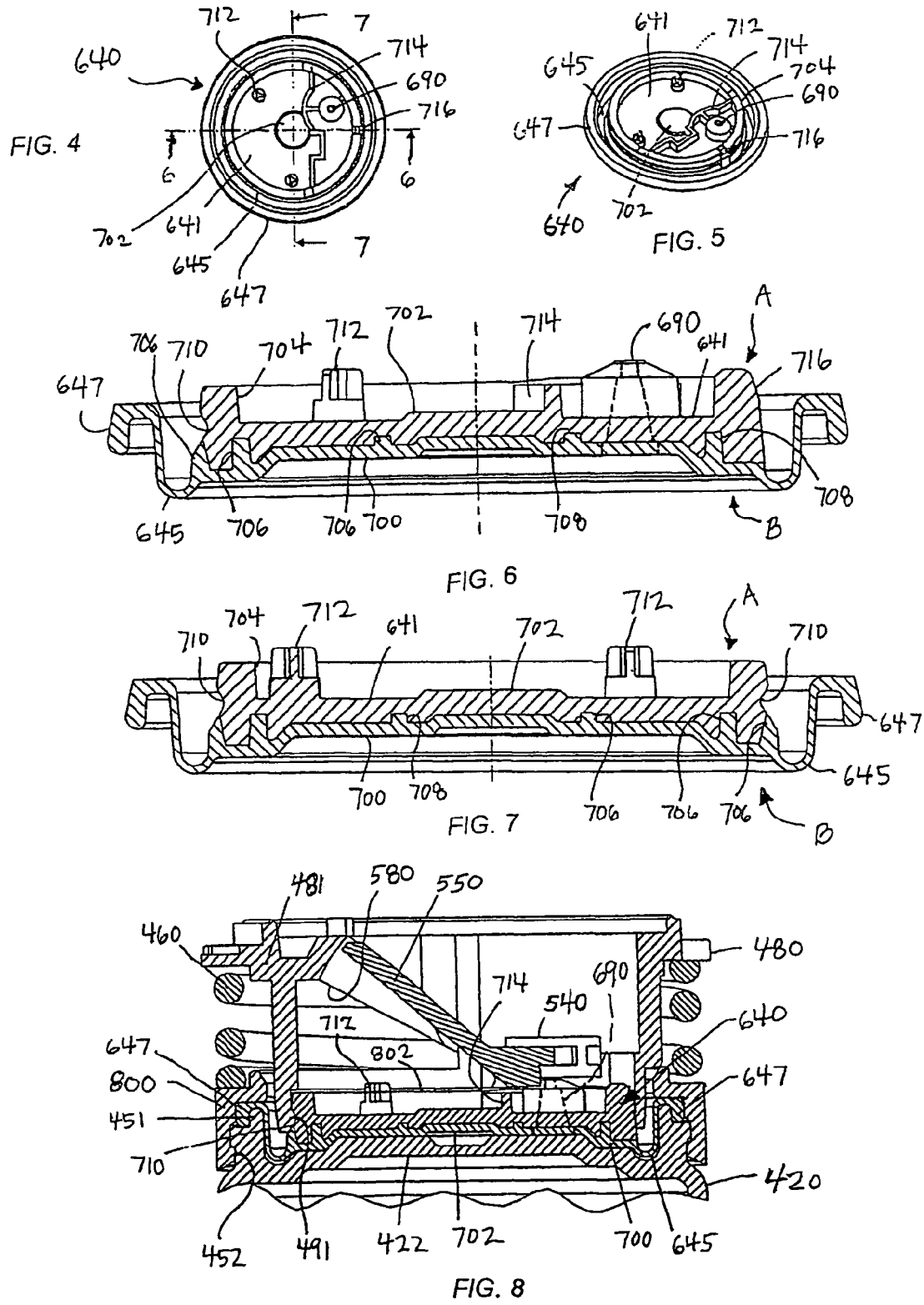

MEDICAMENT DISPENSING DEVICE WITH A MULTIMATERIAL DIAPHRAGM BOUNDING A PNEUMATIC FORCE CHAMBER

CROSS-REFERENCE TO RELATED APPLICATIONS

The present application is a National Stage of International Application No. PCT/USO1/18664, filed Jun. 8, 2001, now abandoned, which is a continuation-in-part of U.S. patent application Ser. No. 09/591,321, filed Jun. 9, 2000, now U.S. Pat. No. 6,553,988 issued Apr. 29, 2003, which is incorporated herein by reference in its entirety.

CROSS-REFERENCE TO RELATED PATENT

The subject matter in this application is related to that in U.S. Pat. No. 5,447,150. That patent is incorporated by reference.

FIELD OF THE INVENTION

This invention relates to a dispensing device, and more specifically, to a device suitable for dispensing discrete amounts of fluid. In particular, the invention is concerned with a dispensing device of the type where the metered dose is administered in response to the inhalation of the patient.

BACKGROUND OF THE DISCLOSURE

Metered dose inhalers are well known in medicine for treatment, or alleviation of the effects of respiratory complaints, for example asthma. Breath-actuated devices are also known, and have been the subject of many patent applications.

GB 1288971; GB 1297993; GB 1335378; GB 1383761; GB 1392193; GB 1413285; WO85/01880; GB 2204799; U.S. Pat. No. 4,803,978 and EP 0186280A describe inhalation-actuated dispensing devices for use with a pressurised aerosol dispensing container. The device includes a dispensing container and the container includes a valve capable of releasing a metered amount of the aerosol contents, when an internal spring operating the valve is compressed by a sufficient amount. The dispensing device often comprises a chamber having a mouthpiece, air inlets, actuating means for causing the actuation of the valve in the dispensing container, a latching means for releasably retaining said metering valve in a charged position, and an inhalation responsive means for releasing the latch, such that a metered amount of aerosol compound is discharged into the region of the mouthpiece. The overall objective is to give co-ordination of discharge of medicament from the aerosol container with inhalation of the patient, thus allowing a maximum dose of medicament to reach the bronchial passages of the lungs.

The latching means is often connected to a valve which moves from a latching position to a dispensing position in response to a partial vacuum developed upon inhalation.

EP-A-0045419 describes an inhalation device having biassing means which are alone of insufficient force to depress the container but which together are of sufficient force to do so.

EP-A-186280 describes a device which employs magnets to control the release of the aerosol container.

U.S. Pat. No. 3,605,738 describes devices in which the aerosol container communicates with the mouthpiece via a metering chamber. A metered quantity of the aerosol compound is discharged into the metering chamber and this is conveyed to the mouthpiece via an inhalation-actuated valve.

GB 1269554 describes a device wherein the aerosol container is moveable by a lever and cam system into a charged position held by a latch, a pressure differential acting to trip the latch and move the valve of the container to a discharge position.

U.S. Pat. No. 5,447,150, incorporated by reference herein, disclosed a metered dose inhaler, wherein the release of the medicament is actuated by the inhalation of the patient. That patent disclosed an inhalation-actuated device which is more simple and compact than the then-prior art dispensers. In one disclosed form, a closed negative pressure region is defined in part by a diaphragm molded from a single material. The diaphragm includes a relatively thick central disk, surrounded by a relatively thin flexure and peripheral ring. That construction is difficult to fabricate, in part due to the differing thickness regions.

SUMMARY OF THE INVENTION

According to one aspect of the present invention there is provided an improved dispensing device for use with a drug delivery system comprising a means for releasing a measured dose of medicament from the system, the releasing means comprising a means for applying a preload capable of actuating the delivery means in the system, a means for applying a resisting pneumatic force capable of preventing actuation of the delivery means and a release device capable of freeing the resisting pneumatic force to allow the preload to actuate the delivery means and dispense the medicament. The means for applying a resisting pneumatic force of the present invention is similar to that in U.S. Pat. No. 5,447,550 but includes a structure that is distinct from, and provides substantial improvement over, the corresponding structure in U.S. Pat. No. 5,447,150.

The pneumatic resisting means of the present invention is provided by air which is held at a negative pressure below atmospheric prior to release. That negative pressure provides a pneumatic resisting force which opposes the preload force. The release device acts to return the pressure to atmospheric or prior equilibrium, thus allowing the full force of the preload to act. The pneumatic resisting force is established by a negative pressure region defined in part by a diaphragm. The diaphragm includes a central disk of a first, relatively high stiffness material and a peripheral ring, coupled by a flexure of a second, relatively low stiffness material. In various forms, the peripheral ring may be of the same material as the flexure, or may be of a different material.

The device is particularly suited for use with pressurized inhalation aerosols having valves as the delivery means.

Although this device has been described in particular relation to a system using air, it will be realized that in a closed system any suitable gas could be used.

In a preferred arrangement, there is provided a breath actuated dispensing device for use with an aerosol medicament container for dispensing a medicament in a metered dose. The container is cylindrical and extends along a container axis between a first end and a second end. The container has a spring based aerosol valve at the first end, which is responsive to an axial force above a predetermined threshold to release the metered dose. The device includes a housing disposed about a central axis and having a first end and a second end, where the second end includes a shoulder and an expulsion nozzle extending therethrough. A support sleeve is disposed within the housing. The sleeve is adapted for axial motion along the central axis. The sleeve is further adapted to support the second end of the container, whereby the container axis is substantially coaxial with the central axis and the aerosol valve is positioned adjacent the shoulder and in communication with the expulsion nozzle.

The device further includes a diaphragm assembly having a relatively rigid central disk, a peripheral attachment ring disposed about a peripheral portion of the disk, and an annular flexure extending between the peripheral portion of the disk and the attachment ring. The central disk is affixed to the first end of the housing and the peripheral ring is affixed to the sleeve, thereby defining a closed region between the diaphragm and the sleeve. A breath actuated valve assembly is provided to selectively establish in a first state an air flow path between the closed region and regions exterior thereto, and interrupting in a second state the air flow path. A spring force bias element is adapted to bias the sleeve toward the second end of the housing. When the breath actuated valve element is in the second state, pneumatic pressure in the closed region establishes a force on the sleeve equal opposite the bias and of a magnitude less than or equal to the bias. In that circumstance, the axial force on the aerosol valve is below the predetermined threshold, and whereby when the breath actuated valve element is in the first state, pneumatic pressure in the closed region establishes a substantially zero force on the sleeve and the bias is sufficient to drive the sleeve and the container toward the shoulder and establish an axial force on the aerosol valve above the predetermined threshold.

Preferably, the central disk is made of a first material characterized by a relatively high stiffness, and the annular flexure is made of a second material characterized by a relatively low stiffness. The annular flexure is bonded to the disk, whereby the disk, the annular flexure and the peripheral ring form a contiguous assembly. In an alternative form, the ring and flexure may be different material as well. Preferably, the multimaterial diaphragm is made using a multishot molding process wherein a first portion (such as the disk) is molded in a first step, and a second portion (such as the flexure and ring) are molded in a second step, and at the same time bonded to the first portion.

It is also preferred that the release device is breath-actuated in order to co-ordinate the release of the medicament with the intake of breath. The favored breath-actuating means comprises a moveable vane mechanism. This vane mechanism may be housed in the upper part of the chamber. A valve seal is preferably attached to said vane, such that on inhalation the vane moves from its rest position to its actuating position, thus moving the valve seal out of contact with the valve port, causing the opening of the valve. The vane mechanism is preferably dynamically balanced, and may be biased towards its closed position, e.g. by a spring. When the valve opens, an air flow path is established between the negative pressure region and regions exterior thereto.

The outer chamber may include air inlets allowing passage of air to the mouthpiece of the device. The inlets may take the form of slots or of an air porous membrane. The latter is particularly suitable to help filter dust.

The medicament may be a drug per se or on any form of carrier, e.g. including a powder or a gaseous carrier.

BRIEF DESCRIPTION OF THE DRAWINGS

For a fuller understanding of the nature and the objects of the invention, reference should be made to the following detailed description and the accompanying drawings in which like reference numerals refer to like elements and in which:

FIG. 4 shows a top plan view of another diaphragm for use with an inhaler according to an embodiment of the invention;

FIG. 5 shows a top perspective view of the diaphragm of FIG. 4;

FIG. 6 shows a sectional view of the diaphragm taken along lines 6-6 of FIG. 4;

FIG. 7 shows a sectional view of the diaphragm taken along line 7-7 of FIG. 4; and FIG. 8 shows an enlarged section view of the diaphragm of FIG. 4 in position in a pre-actuated state within an actuator assembly of an inhaler according to an embodiment of the invention.

DESCRIPTION OF THE PREFERRED EMBODIMENTS

Figure 1:
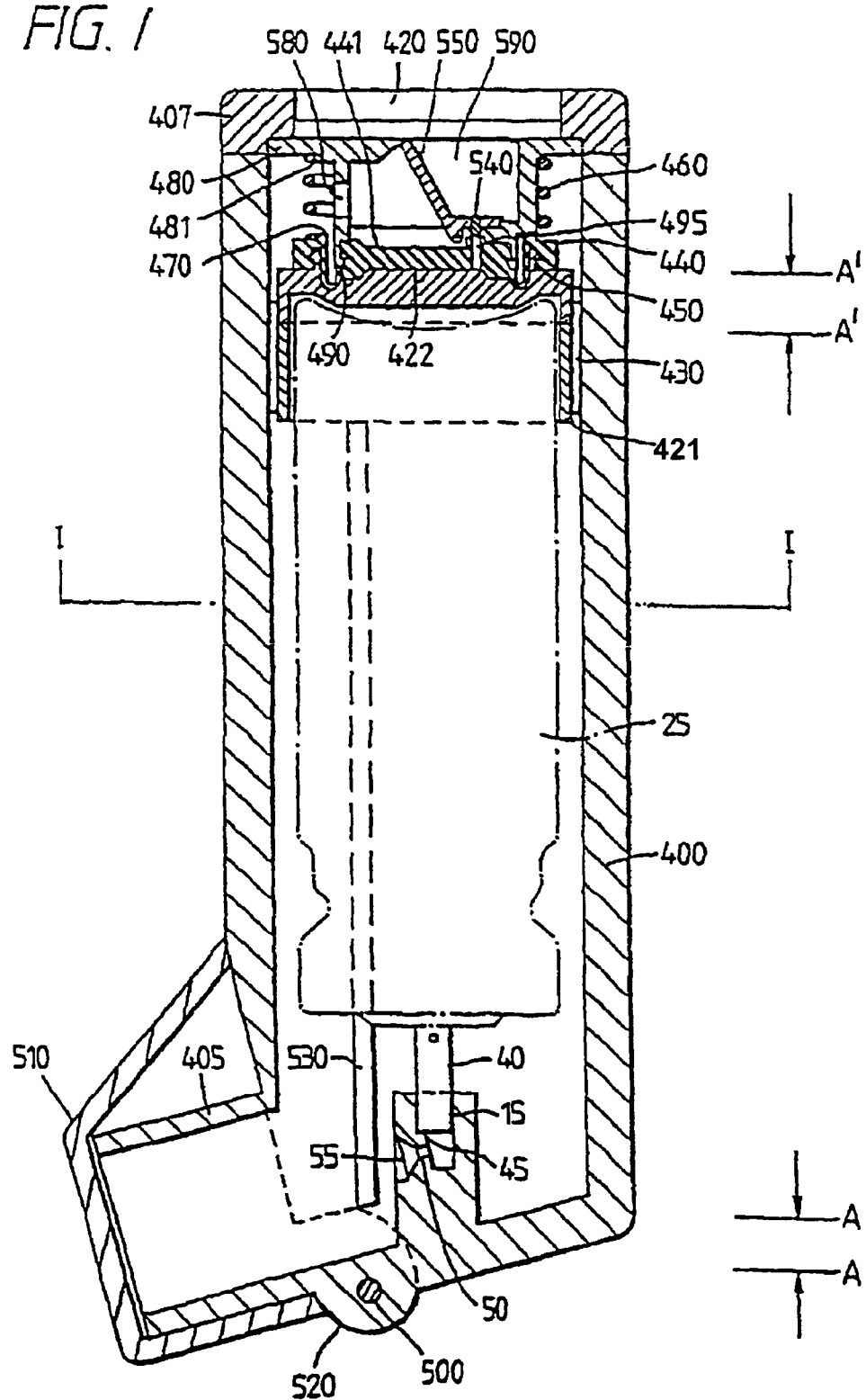
FIG. 1 is a section view of an inhaler according to an embodiment of the invention.

In an arrangement as shown in FIG. 1, an inhalation device consists of a main body 400, which is generally cylindrical in cross section, with a mouthpiece section 405 at one end and an end cap 407 housing air inlets 420 at the other end. A known type of aerosol dispensing container 25 of generally cylindrical shape is housed within the main body of the device. The aerosol dispensing container has a stem 40 which contains an aerosol dispensing valve (not shown). The bore 15 is such that it forms an air tight seal on the stem 40 of the aerosol dispensing container 25. A shoulder 45 limits and locates the position of the stem 40, which in turn locates the aerosol dispensing container 25 in position in the main body 400. A passage 50 extends from the bore 15, continuing from the shoulder 45 to interconnect with a dispensing nozzle 55.

The opposite end of the dispensing container is contained within a sleeve 421 of similar cross section to the main body 400. The longitudinal axis of both the sleeve 421 and main body 400 is generally coaxial. The sleeve is in loose sliding contact with the inner wall of the main body and may include several rebated grooves 430 in its walls to allow free passage of air in the main body past the sleeve. The sleeve 421 may be held in place by connection with a diaphragm 440 held in connection with the top of the main body 400, as will now be described. Thus, the sleeve 421 effectively hangs from the top of the main body.

One end of an e.g., molded flexible diaphragm 440 (as shown alone in FIG. 2) comprising a rigid disc-like section 441, a flexible generally cylindrical wall section 445 and a diaphragm connection section 447, is fitted around a inner sleeve groove 450 in the sleeve, e.g. by snap-fitting. A further molded lip 470 on the diaphragm 440 provides a snug fit for one end of a compression spring 460. The compression spring is thus located and free to act on the sleeve. The other end of the compression spring is located by an annular shoulder 481 in a predominantly cylindrical flanged insert 480 housed in the top section of the main body 400. This insert includes a groove 490 into which the disc-Like section 441 of the flexible diaphragm 440 is snap-fitted. Preferably, the multimaterial diaphragm is made using a multishot molding process wherein a first portion (such as the disk) is molded in a first step, and a second portion (such as the flexure and ring) is molded in a second step, and at the same time bonded to the first portion.

Figure 2:
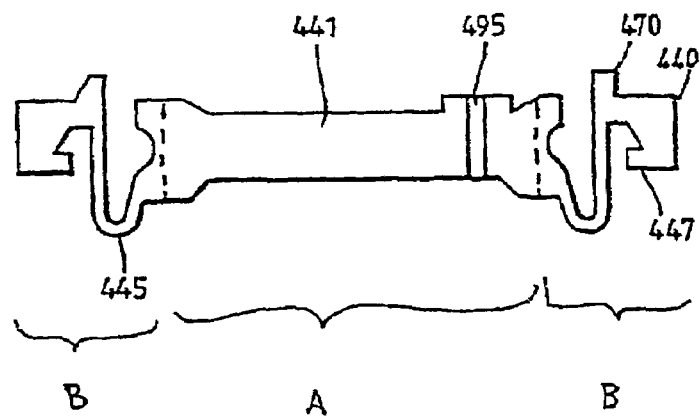
FIG. 2 shows an enlarged view of a diaphragm for use with the embodiment shown in FIG. 1.

With the improved diaphragm configuration of the invention, shown in FIG. 2, the relatively thick disk-portion "A" is molded from a rigid material (relatively high stiffness), which is particularly resistant to flexural deformation when the closed region 600 is at negative pressure, while the relatively thin flexure portion "B" is molded from an optimally flexible (relatively low stiffness) material, minimising the force required to move the inner sleeve and hence the forces required to be stored and released by the mechanism. The relatively thin flexure portion "B" is bonded to the diskportion "A" along a continuous surface substantially parallel to the central axis of the diaphragm.

The joint between the diaphragm connector section 447 and inner sleeve groove 450 is arranged to be air tight and the shape of the top surface of the sleeve 422 to conform to the internal shape of the diaphragm such that in the rest position of the inhaler the two surfaces are in close proximity, and the enclosed space between them very small.

The cylindrical flanged insert 480 is retained in place by the end cap 407 fitted into the main body of the device. This forms a chamber 590 between the air inlet slots 420 and the rigid part 441 of the diaphragm. The chamber is provided with one or more air pathways 580 such that air may pass from the air inlet slots 420 to the mouthpiece 405. The rigid disc-like section 441 of the diaphragm also includes a small valve port 495 which is normally covered by a valve seal (flap) 540 housed in a vane 550 pivotally connected to the cylindrical flanged insert 480.

The vane 550 in its rest position divides the chamber 590 between the air inlets 420 and the air pathways 580 that link to the mouthpiece such that it may move from its rest position by means of a pressure drop between the air inlets and the mouthpiece. On movement of the vane to the actuated position the valve seal (flap) 540 is sufficiently moved to open the valve port 495. (The vane 550 may be biased closed by a light spring flexure, a weight or a magnet not shown.)

As shown in FIG. 1, the end of the main body having a pivot 500 has a recess adapted to receive a cam 520 integral with a dust cap 510 operating on the pivot. The recess further includes a passage communicating with a similar passage molded into the internal wall of the main body 400. A camfollower 530 extending from the lower edge of the inner sleeve 421 acts on the cam such that when the dust cap is in the closed position the inner sleeve is forced by the camfollower to its uppermost position.

When the dust cap is rotated to its open position the cam profile is such that the camfollower is free to move downwards by an amount sufficient to allow actuation of the device.

In its rest position the dust cap 510 is closed, the camfollower 530 restrains the inner sleeve 421 in its uppermost position such that the enclosed space trapped between the diaphragm 440 and the top surface 422 of the inner sleeve is at a minimum and the spring 460 is compressed. The valve port 495 is closed by the valve seal (flap) 540 and the sleeve 421 is clear of the top of the aerosol can 25 which is thus unloaded.

Figure 3:
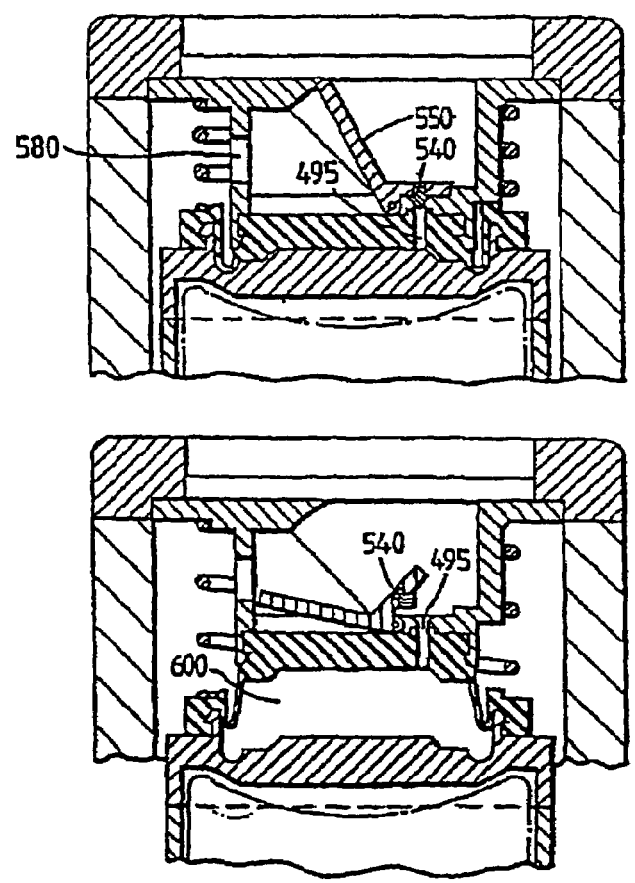
FIG. 3 shows an enlarged section view of the diaphragm in position in pre-actuated and actuated state.

The dust cap is opened rotating the integral cam 520 allowing the camfollower 530 to drop by amount AA. The inner sleeve is forced downwards under the action of the spring 460. As the inner sleeve moves downwards the enclosed volume between the diaphragm 440 and inner sleeve is increased by a linear equivalent amount A'A', less than or equal to AA. Since the valve port 495 is closed this creates a low pressure volume or near vacuum in the closed region 600 [FIG. 3]. The effect of the pressure differential between the closed region 600 and atmospheric pressure is such that the inner sleeve tends to resist the action of the spring. As the inner sleeve moves downwards it contacts the aerosol can 25 and begins compression of the aerosol valve (not shown).

Downward movement of the inner sleeve will continue until there is a balance of forces between the compressive force in the spring 460 and resisting forces created by the pressure differential and compression of the aerosol valve. The geometry of the device is arranged such that this balance occurs before the aerosol valve has been sufficiently compressed to actuate it.

A typical Chlorofluorocarbon (CFC) aerosol medicament container requires about 20N force to actuate, while a typical hydrofluoroalkane (HFA) aerosol medicament container requires about 40N force to actuate. Thus, depending upon the application, the spring 460 should provide a force 10% to 50% greater than the required actuation force of the medicament container. As is known, CFC containing propellants have been shown to liberate chlorine in the stratosphere and cause ozone depletion. Because of this danger, the Montreal Protocol was signed that bans the use of CFCs. Metered-dose inhalers (MDIs) for treating asthma and other respiratory diseases were exempted from this general ban, although this exemption is temporary and will be lifted as substitute products become available. The first such substitute, HFA propellant, has been on the market for about a year.

It may also be possible to arrange for the balance of forces to take place before the inner sleeve has contacted the aerosol can, such that the spring force is balanced by the resisting force produced on the inner sleeve by virtue of the pressure differential.

On inhalation by the patient through the mouthpiece 405, a small pressure differential is created across the vane 550 which is pivoted towards one end. The pressure differential causes the vane to move from the rest position to the actuated position. The vane 550 and design of the air passageway 580 in the chamber 590 are such that in the actuated position air can flow freely from the air inlets 420 to the patient.

The movement of the vane 550 causes the valve seal (flap) 540 to be moved out of a sealing position with the valve port 495. Opening the valve port allows air into the closed region 600 between the diaphragm and inner sleeve such that the enclosed space reaches atmospheric pressure. This causes an imbalance of forces acting on the sleeve 421 and container 25. The sleeve and container are thus forced downwards by the spring 460 resulting in the release of a measured dose of medicament through the dispensing nozzle 55 and into the mouthpiece at the same time as the patient breathes in. Thus, the patient inhales air with a metered dose of medicament.

After the inhalation of the dose by the patient, the dust cap 510 is returned to its closed position. This rotates the cam 520 and causes the camfollower 530 to be forced upwards. This in turn acts on the inner sleeve 421 moving it upwards to compress the spring 460 and close the closed region 600 between the diaphragm and inner sleeve top surface 422. This forces air out of the closed region 600 which escapes through the valve port 495 lifting the valve seal (flap) 540. Since the valve seal (flap) is only lightly biased to its closed position it presents little resistance to air flow out of the enclosed space. The aerosol can is free to return to the rest position under the action of its own aerosol valve spring.

In use the patient loads the aerosol dispensing container into the main body. The aerosol container may be loaded by providing a coarse threaded screw in the main body 400, for example about the line I-I. When part of the main body 400 has been unscrewed, the aerosol can be inserted. The main body 400 can then be replaced locating the inner sleeve over the top end of the can, and the device is ready for use. As described previously, the device could be manufactured as a sealed unit.

The device may be provided with means to provide a regulated air flow to the user or inhaler. Thus a sonic device, e.g., a reed, may be provided which sounds when the inspired air flow is greater than a pre-set level, e.g., above 30 to 50 liters per minute. The sonic device may be located in the mouthpiece 95 or below the air inlet 421. The sound produced warns the patient to breathe at a lower rate.

The device may also be provided with a means such that it will not operate below a certain pre-determined air flow rate, e.g. 10 to 30 liters per minute. In one embodiment the vane 550 will be biased by a spring such that the predetermined minimum air flow is necessary for it to move to its actuated position and enable the valve seal to open.

The main body of a dispensing device, as described in the above embodiment of this invention is preferably manufactured from a plastic such as polypropylene, acetal or moulded polystyrene. It may however be manufactured from metal or another suitable material.

Referring to FIGS. 4-8 another diaphragm assembly 640 and actuator assembly according to the present invention for use with the medicament dispenser of FIG. 1 are shown. The diaphragm assembly 640 and the actuator assembly of FIGS. 4-8 are similar to the diaphragm assembly 440 and the actuator assembly of FIGS. 2 and 3, such that similar elements are provided with the same reference numerals.

The molded flexible diaphragm 640 includes a rigid disc-like section 641, a flexible generally cylindrical wall section, or annular flexure 645, and a thicker connector section, or peripheral attachment ring 647. A central portion 700 is unitarily formed with and extends radially inwardly from the annular flexure 645. The central portion preferably is provided in the form of a central portion 700 bonded along a top surface to a bottom surface of the rigid disc-like section 641, i.e., surfaces substantially traverse to the central axis of the diaphragm 640.

Referring to FIGS. 6 and 7, the relatively thick disk-portion "A" which includes the disc-like section 641 of the diaphragm 640, is molded from a rigid material (relatively high stiffness) such as Acrylonitrile Butadiene Styrene (ABS), which is particularly resistant to flexural deformation when the closed region 600 is at negative pressure. The relatively thin flexure portion "B" which includes the central portion 700, the annular flexure 645 and the peripheral attachment ring 647, is molded from an optimally flexible material (relatively low stiffness) such as a thermoplastic elastomer (TPE), permitting high performance. Preferably, the multimaterial diaphragm 640 is made using a multishot molding process wherein the first portion "A" is molded in a first step, and the second portion "B" is molded in a second step, and at the same time bonded to the first portion.

As shown in FIGS. 4 through 7, the central portion 700 and the rigid disc-like section 641 both define a central upwardly extending boss 702 for additional strength. In addition, the rigid disc-like section 641 includes an outer axial wall 704 which provides further strength to the diaphragm 640. The central portion 700 includes axial walls 706 which are received within and bonded to axial grooves 708 of the rigid disc-like section 641, thereby providing bonding surfaces substantially parallel with the central axis of the diaphragm 640 and increasing the total bonding surface area between the central portion 700 and the rigid disc-like section 641.

Referring also to FIG. 8, the peripheral attachment ring 647 of the diaphragm 640 is fitted around an annular wall 451 of the sleeve 421 and is secured in an air-tight manner thereon with a retainer ring 800, which is secured to the sleeve 421, e.g., by snap-fitting into an annular groove 452 of the sleeve. The retainer ring 800 also provides a snug fit for one end of the compression spring 460, such that the compression spring is thus located and free to act on the sleeve 421. The cylindrical flanged insert 480 housed in the top section of the main body 400 of the inhaler includes a protrusion 491 which is snap fit into a radially outwardly facing circumferential groove 710 of the relatively rigid disc-like section 641 of the flexible diaphragm 640.

The valve port 690 of the diaphragm 640 passes through the rigid disc-like section 641 and the central portion 700 of the diaphragm. The valve port 690 is closed by the valve seal (flap) 540, which is biased closed by a flat spring 802, as shown in FIG. 8. The rigid disc-like section 641 of the diaphragm includes protrusions 712 extending upwardly therefrom that receive and correctly position the flat spring 802. The rigid disc-like section 641 of the diaphragm 640 also includes a baffle 714 on a top surface thereof for substantially preventing air flow between the valve seal (flap) 540 and the diaphragm. The baffle 714 closely follows the profile of the underside of the flap 540, yet provides sufficient clearance for the flap to open upon breath-actuation. The rigid disc-like section 641 of the diaphragm 640 additionally includes an assembly location key 716 for use in correctly assembling the diaphragm 640 within the actuator assembly of FIG. 8.

The invention may be embodied in other specific forms without departing from the spirit or essential characteristics thereof. The present embodiments are therefore to be considered in all respects illustrative and not restrictive, the scope of the invention being indicated by the appended claims rather than by the foregoing description, and all changes which come within the meaning and range of equivalency of the claims are therefore intended to be embraced therein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A dispensing device for dispensing a medicament in metered doses, comprising:
   a main body with a first and second end;
   a sleeve movably positioned within said main body and having a closed end;
   a diaphragm assembly including a relatively rigid central disk, a peripheral attachment ring disposed about a peripheral portion of said disk, and an annular flexure extending between said peripheral portion of said disk and said attachment ring, wherein said central disk is affixed to said first end of said main body and said attachment ring is affixed to said sleeve, thereby defining a closed region between said diaphragm assembly and said closed end of said sleeve, said diaphragm assembly also including a valve port providing fluid communication between said first end of said main body and said closed region;
   a spring operatively positioned in said main body to apply a preload force to said sleeve; and
   a vane operatively positioned in said main body and movable between first and second positions, wherein when said vane is in said first position said vane seals said valve port of said diaphragm assembly and when said vane is in said second position said valve port is unsealed; wherein said central disk of said diaphragm assembly comprises a first material characterized by a relatively high stiffness, said annular flexure comprises a second material different from said first material and characterized by a relatively low stiffness, said annular flexure is bonded to said disk along a continuous surface substantially parallel to a central axis of said diaphragm assembly, and said disk, said annular flexure and said attachment ring form a contiguous assembly.

2. A dispensing device according to claim 1 wherein said annular flexure is bonded to said disk along at least one surface substantially transverse to said central axis.

3. A dispensing device according to claim 2 wherein said diaphragm assembly further includes a central portion comprising said second material and unitarily formed with and extending radially inwardly from said annular flexure, said central portion bonded to said disk along said at least one surface substantially transverse to said central axis.

4. A dispensing device according to claim 3 wherein said central portion comprises a disk.

5. A dispensing device according to claim 3 wherein said central portion is also bonded to said disk along at least one surface substantially parallel to said central axis.

6. A dispensing device according to claim 5 wherein said central portion includes at least one annular wall coaxially arranged with respect to said central axis and received within an annular groove of said disk, said annular wall bonded to said disk along the at least one surface substantially transverse to said central axis.

7. A dispensing device according to claim 3 wherein said diaphragm assembly includes a valve port providing fluid communication with said closed region between said diaphragm assembly and said sleeve, and wherein said valve port passes through said central portion and said disk.

8. A dispensing device according to claim 3 for dispensing an aerosol medicament in metered doses.

9. A dispensing device according to claim 3 for dispensing an HFA aerosol medicament in metered doses.

10. A dispensing device according to claim 3 for dispensing a dry powder medicament in metered doses.

11. A dispensing device according to claim 3 for dispensing an aqueous medicament in metered doses.

12. A dispensing device for dispensing a medicament in metered doses, comprising:

a main body with first and second ends;

a sleeve movably positioned within said main body and having a closed end;

a diaphragm assembly including a relatively rigid central disk having an outer peripheral wall in an unassembled condition of said diaphragm assembly, said outer peripheral wall being substantially parallel to a central axis of said diaphragm assembly, a peripheral attachment ring disposed about the outer peripheral wall of said disk in an assembled condition of said diaphragm assembly, and an annular flexure having an inner peripheral wall in an unassembled condition of said diaphragm assembly, said inner peripheral wall being substantially parallel to the central axis of said diaphragm assembly, and a substantially continuous bond between said inner peripheral wall of said annular flexure and said outer peripheral wall of said disk in said assembled condition of said diaphragm assembly;

said disk being affixed to said first end of said main body and said attachment ring being affixed to said sleeve, thereby defining a closed region between said diaphragm assembly and said closed end of said sleeve;

a valve port in said diaphragm assembly providing fluid communication between said first end of said main body and said closed region;

a spring operatively positioned in said main body to apply a preload force to said sleeve; and a vane operatively positioned in said main body and movable between first and second positions, wherein when said vane is in said first position said vane seals said valve port of said diaphragm assembly and when said vane is in said second position said valve port is unsealed;

wherein said central disk of said diaphragm assembly comprises a first material having a relatively high stiffness, and said annular flexure comprises a second material having a relatively low stiffness.

* * * * *

UNITED STATES PATENT AND TRADEMARK OFFICE
CERTIFICATE OF CORRECTION

PATENT NO.       : 7,637,260 B2                              Page 1 of 1
APPLICATION NO. : 10/276531
DATED            : December 29, 2009
INVENTOR(S)      : Michael Holroyd It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 876 days.

Signed and Sealed this

Twenty-first Day of December, 2010

David J. Kappos
*Director of the United States Patent and Trademark Office*